United States Patent [19]
McKenzie et al.

[11] Patent Number: 5,877,146
[45] Date of Patent: Mar. 2, 1999

[54] THERAPEUTIC USE OF HEMOGLOBIN IN THE TREATMENT OF BLOOD VESSEL BLOCKAGE

[75] Inventors: Jack E. McKenzie, McLean, Va.; Kenneth E. Burhop, Mundelein, Ill.

[73] Assignee: Baxter International Inc., Deerfield, Ill.

[21] Appl. No.: 511,763

[22] Filed: Aug. 7, 1995

Related U.S. Application Data

[63] Continuation of Ser. No. 218,536, Mar. 28, 1994, abandoned.

[51] Int. Cl.⁶ .................................................. A61K 38/04
[52] U.S. Cl. ...................................................... 514/6
[58] Field of Search ...................................... 514/6

[56] References Cited

PUBLICATIONS

Lutz et al., Oxygen Transport to Tissues XII, Edited by J. Piiper et al. Plenum Press, NY 1990. pp. 683–690.

*Primary Examiner*—Josë G. Dees
*Assistant Examiner*—Mary C. Cebulak
*Attorney, Agent, or Firm*—Senniger, Powers, Leaviit & Roedel

[57] ABSTRACT

Administration of low doses of hemoglobin minimizes damage to the myocardium after blockage and significantly reduces reperfusion injury. Hemoglobin exerts a pharmacological effect by increasing perfusion and blocking the molecular events leading to permanent injury following an ischemic episode.

11 Claims, 3 Drawing Sheets

THERAPEUTIC USE OF HEMOGLOBIN IN THE TREATMENT OF BLOOD VESSEL BLOCKAGE

This is a continuation of application Ser. No. 8/218,536, filed on Mar. 28, 1994, now abandoned.

BACKGROUND OF THE INVENTION

The blockage of an arterial vessel produces ischemia in the tissue normally nourished by the occluded vessel. If the blockage is removed permitting reperfusion of the affected area after greater than sixty minutes of ischemia, further injury called reperfusion injury is paradoxically observed. This reperfusion injury is associated with a number of biochemical and physiological events such as release of intracellular enzymes, transient rise in blood pressure, reduction in contractility, influx of calcium, disruption of cell membranes, and eventual tissue necrosis (see Ferrari, et al., *Am. J. Clin. Nutr.* 53:215S (1991). It is thought that much of the tissue damage arising during ischemia and reperfusion results from the chemical action of excess amounts of oxygen free radicals which have accumulated (Lefer, et al., *Basic Res. Cardiol.,* 86 Suppl. 2:109 (1991) and Kirsh, et al., *J. Neurotrauma,* 9 Suppl. 1:S157 (1992), and Bolli, *Cardiov. Drugs & Ther.,* 5:249 (1991).

Experiments in a number of animal models have investigated the use of antioxidants or enzymes to control reperfusion injury. For example, Weyrich, et al., *Circulation,* 86:279 (1992) showed that administration of L-arginine reduced necrotic injury in a cat model of myocardial infarction. McMurray et al., *J. Clin. Pharmac.,* 31:373 (1991) investigated sulfhydryl containing angiotensin converting enzyme inhibitors. Naslund, et al., *Circ. Res.,* 66: 1294 (1990) concluded from their work on a swine coronary model, that infarct size could by limited by administration of superoxide dismutase, but only during a very narrow window of time post-infarction. Schaer, et al., *JACC,* 15:1385 (1990) report a reduction in reperfusion injury by administering an acellular oxygenated perfluorochemical emulsion called Fluosol.

An important model system is percutaneous transluminal coronary angioplasty in the pig. McKenzie, et al., *Biomat., Art., Cells & Immob. Biotech.,* 20:2 (1992) utilized this technique to study the effects of temporary regional myocardial ischemia. They inserted a catheter into the proximal left anterior descending coronary artery and inflated the catheter balloon to occlude the artery for a period of 4 minutes. A significant reduction in cardiac function is reported compared to controls as measured by mean arterial blood pressure (MAP), peak systolic left ventricular pressure (IVP), rate of left ventricular pressure development (dP/dt), pressure rate product (PRP), and cardiac output (CO). In addition, electrocardiograms showed depression of the S-T segment of the ECG. These experiments are significant because McKenzie, et al. compared controls to animals receiving infusions of hemoglobin, and found that cardiac function and S-T segment ECG both increased significantly.

The concept of infusing hemoglobin products as a substitute for blood has a long history (for a historical perspective, see R. M. Winslow, "Hemoglobin-based Red Cell Substitutes", The Johns Hopkins University Press, 1992). Free hemoglobin is not suitable for this purpose since oxygen is bound too tightly to be released in the tissues. Also, hemoglobin monomers are rapidly cleared from the blood and exhibit renal toxicity. Better success has been achieved with chemically modified hemoglobins, which assume a conformation allowing release of oxygen, and whose size and stability are more resistant to clearance.

Hemoglobins may be alpha alpha crosslinked as disclosed in U.S. Pat. Nos. 4,600,531 and RE 34,271 (Walder), and virus inactivated and purified as taught in U.S. Pat. No. 4,861,012 (Estep). Modification by pyridoxyation, carbamylation, carboxymethylation, are also known, as are chemical schemes for both cross-linking and polymerizing, as by glutaraldehyde. A summary of these chemistries is contained in Winslow, supra.

SUMMARY OF THE INVENTION

This invention provides a method for treating blockage of a blood vessel, which may be a thrombus, fat embolus, plaque, or other obstruction, which comprises administering, generally by intravenous infusion, hemoglobin to a patient undergoing tissue ischemia. There are different ways of defining the therapeutically efficacious dose which may be administered. An amount of hemoglobin may be administered which is sufficient to suppress or reduce reperfusion injury to the tissue whose nourishment has been disrupted by the blockage. That amount is generally an amount which minimally raises mean arterial blood pressure 5 to 15 percent above the preadministration base line value.

Blood pressure elevation is a secondary effect of hemoglobin administration, but it is useful as a surrogate measure for monitoring doses in the permissive range sufficient for suppressing reperfusion injury in a patient undergoing ischemia. The dose range may be from 10 to 2500 mg/kg of body weight.

The benefits and objects of administering hemoglobin as a treatment for blood vessel blockage are that it increases perfusion to the area at risk, it stabilizes the circulatory system, as in cardiac ischemia, and may act directly or indirectly to lower levels of free oxygen radicals and other molecular species associated with tissue damage. While increased perfusion is readily observable, many of hemoglobin's pharmacological properties are not yet understood mechanistically. It would appear that some of these properties are unrelated to oxygen-carrying capacity since the effects are exerted in too low doses to make much of a predicted impact on total oxygen delivery.

DETAILED DESCRIPTION OF THE PREFERRED EMBODIMENT

Figure 1A:
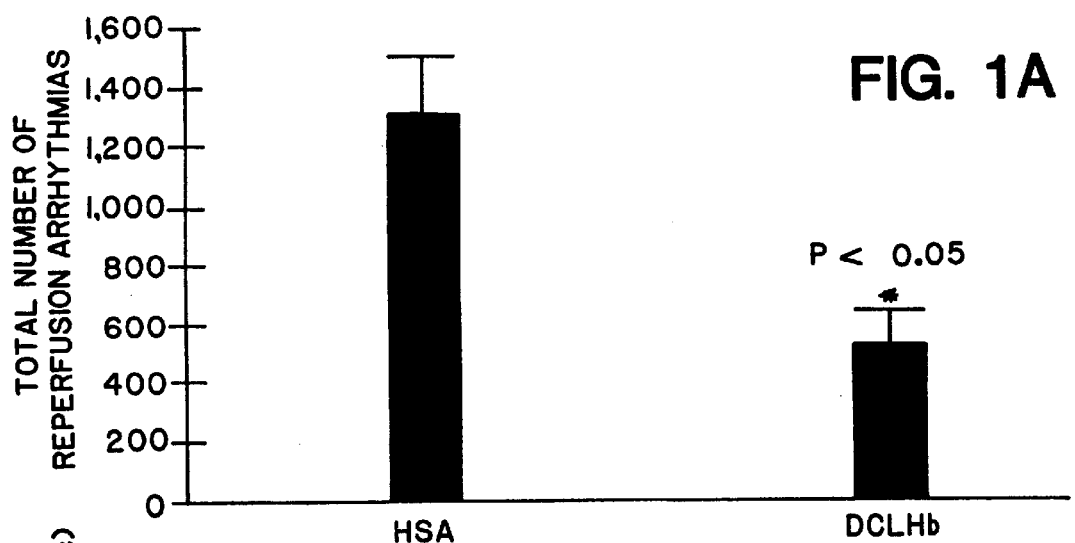
FIG. 1A. Effects of human serum albumin (HSA) and diaspirin crosslinked hemoglobin (DCLHb™) on the total number of reperfusion arrhythmias. The number of arrhythmias are counted from beginning of reperfusion for 45 minutes. Values are means ±SEM. *Significantly different from HSA (P<0.05).

The blockage of blood vessels may occur by any one of several mechanisms including degenerative plaque, thrombosis, fat embolus, clot, and may occur in many tissues and locations of the body. The effect of such blockage is to impair or completely curtail blood flow to the portions of the vessel downstream from the blockage. The tissue nourished by the occluded vessel is thus deprived of oxygen and nutrients, and cell death may ensue. In situations where the affected vessel is a coronary artery or an artery which serves a vital brain or other organ function, the blockage may be life-threatening.

Reperfusion therapy utilizing hemoglobin is effective when some degree of blood flow is restored, or in situations in which collateral blood flow can take advantage of the increase in perfusion resulting from hemoglobin administration. Where occlusion of the blood vessel is essentially complete, restoration of flow may occur spontaneously, may be supported by administration of thrombolytic enzymes such as streptokinase or tissue plasminogen activator, or by surgical intervention and angioplasty.

The dosage of hemoglobin utilized in reperfusion therapy varies from patient to patient, but generally will fall in the range from 10 to 2500 mg/kg of body weight. The preferred dose is a low dose, meaning that it is an amount too low to contribute any substantial additional oxygen-carrying capacity to the circulatory system. It is believed that hemoglobin increases perfusion pharmacologically to achieve its primary beneficial effects. Increased perfusion may result from more efficient utilization of the venous blood supply, particularly in situations involving blood loss. However, the dramatic limiting of reperfusion injury and consequent reduction of permanent cell damage in the area at risk cannot presently be fully explained, and Applicants therefore do not wish to be bound to any particular theory.

Ideally, a physician will administer an amount of hemoglobin which confers the desired effect of optimally suppressing reperfusion injury and minimizing permanent cellular damage. This amount has been determined empirically as falling within 10 and 2500 mg/kg of body weight. As a practical matter, the physician can administer hemoglobin in increments until the mean arterial blood pressure has attained a value about 5 to 15 percent above the hemoglobin preadministration base line. Applicants now understand that increase in perfusion and the well-known pressor effect of hemoglobin are not necessarily causally linked, because suppression of the pressor effect by drugs such as prazosin does not impair the observed increase in perfusion. However, pressor activity can be used as a surrogate indicator to ensure that the patient has received enough hemoglobin to achieve the desired perfusion increase, which is difficult to measure directly in the clinic.

The timing of administration should preferably be at the time of or as soon as possible after the condition of blockage is first diagnosed. Treatment out to several hours after the onset of blockage may be beneficial particularly when the blood vessel involved impacts a relatively small area at risk. In the case of cardiac blockage, a relatively small area at risk would involve about 5 to 25 percent of the myocardium.

The hemoglobin utilized in reperfusion therapy may be any type for which the indicator pressor effect is observed and which has the following general properties: normal or near-normal oxygen carrying and release properties, stroma-free, non-antigenic and non-pyrogenic (i.e. less than 0.25 endotoxin units per milliliter), and be free of bacterial and viral contamination. In addition, the hemoglobin preparation should have the colloid and oncotic properties of blood. The hemoglobin may be isolated as disclosed in U.S. Pat. Nos. 4,439,357, 4,526,715, 4,598,064, and 4,600,531 hereby incorporated by reference. The hemoglobin is preferably rendered virus free, as disclosed in U.S. Pat. No. 5,281,579, incorporated by reference.

The preferred hemoglobin is maintained in stable oxygen-releasing conformation by crosslinking. The best method of crosslinking involves a lysine-lysine bridge between the alpha subunits, as disclosed in U.S. Pat. Nos. 4,600,531 and RE 34,271. Because the tetramer cannot fall apart, thereby retaining its 64,000 molecular weight, clearance from the blood stream is slowed. Further lengthening of blood retention time is effected by polymerizing the hemoglobin tetramers, as by polyamide linking groups disclosed in co-owned U.S. application Ser. No. 08/173,882. Alternative crosslinking and polymerizing techniques are described in Winslow, supra. One interesting technique involves simultaneous crosslinking and polymerizing with glutaraldehyde as disclosed in U.S. Pat. No. 5,194,590.

Other advantages of the present invention will be apparent from the Example, which follows.

EXAMPLE 1

An animal model system involving coronary occlusion was used to study the effect of hemoglobin perfusion therapy on controlling tissue damage resulting from sustained ischemia and reperfusion injury. The swine model is the model of choice because numerous studies have shown that the pig heart most closely resembles the human heart physiologically. For a review, see M. M. Swindle, ed., "Swine as Models in Biomedical Research", *Iowa State University Press,* (1992).

One particularly important criterion is the comparable absence in both the pig and humans of collateral flow. Collateral flow is the ability of the capillary bed of one arterial branch to compensate for an occlusion in another branch. The pig heart most closely resembles the human heart in showing a low degree of collateral flow capacity. See Bloor, et al., "The Pig as a Model of Myocardial Ischemia and Gradual Coronary Artery Occlusion", in *Swine as Models in Biomedical Research,* supra.

Experimental Preparation. Yorkshire swine of either sex (n=15), weighing 21.3±1.4 kg, were initially sedated with Ketamine (10 mg/kg, i.m.) to allow placement of an intravenous catheter in an ear vein. Anesthesia was obtained with Pentobarbital Sodium (Nembutal) 30 mg/kg, bolus i.v. injection, with a dose of 31.5 mg/hour given by continuous i.v. infusion, at a rate of 6.3 ml/hour (Sage Instruments Pump), to maintain a surgical plane of anesthesia. The swine were intubated and ventilated (Harvard Respirator). Respiratory status was monitored periodically with arterial blood gas determinations and ventilation rate and/or oxygen flow rate were adjusted to achieve physiological blood gas values. Bilateral femoral cutdowns were performed and the right femoral artery was cannulated with a 9F sheath (Cordis) and a 6F pigtail catheter was advanced under fluoroscopic guidance into the left ventricle. A right carotid cutdown was performed and the right carotid artery was cannulated with a 9F sheath. Three thousand units of Heparin sodium were administered intravenously and repeated doses of 1,000 units were given every 30 minutes. A bolus of 1 mg/kg of lidocaine was given i.v. and an infusion of 50 µg/kg/min was maintained throughout the experiment. Intravenous nitroglycerine was infused to achieve a 5–10 mmHg reduction in blood pressure during guide wire and balloon placement but was discontinued prior to balloon inflation.

Electrocardiograph, blood pressure, and temperature monitoring was performed throughout the experiment.

A 7F AR2 guiding catheter (Scimed) was advanced to the left main coronary artery. Catheter position was confirmed and angiograms were performed using hand injections of 1–5 cc of iodinated contrast (Renografin-76). A 0.014 inch Hi-Torque floppy guide wire (Advanced Cardiovascular Systems) was advanced into the first obtuse marginal branch of the circumflex coronary artery. A Hartzler ACX II® (2 mm diameter, 10 mm length) balloon angioplasty catheter (Advanced Cardiovascular Systems) was advanced over the guide wire into the first marginal branch. Care was taken to assure that the balloon did not obstruct flow in the main circumflex coronary artery. The balloon was inflated with just enough pressure to insure complete occlusion (2–4 ATM) of the first marginal branch for 90 minutes. Occlusion was confirmed by angiography.

Study Protocol. Prior to instrumentation the swine were randomized into one of two study groups. Ten minutes prior to balloon deflation the swine were intravenously infused at 5 ml/kg given over a five minute period (1 ml/kg/min) with either 10% diaspirin crosslinked hemoglobin (DCLHb™) or a Human Serum Albumin (HSA) solution which was oncotically matched to the hemoglobin solution (approximately 8% albumin). At ninety minutes the balloon was deflated and withdrawn. The animal was then allowed to reperfuse for 3 hours. An angiogram was performed after the 3 hour reperfusion period to document vessel patency. The animals were euthanized and the hearts rapidly removed.

ECG Recording. All pigs were instrumented with leads I, II, III, aVr, aVl, aVf, and the precordial lead $V_4$. The total number of arrhythmias were counted from the start of reperfusion to 45 minutes post-reperfusion. The time to onset of arrhythmias was measured from start of reperfusion to the onset of reperfusion arrhythmias. The total duration of the reperfusion arrhythmia period was calculated as the amount of time from the onset of reperfusion arrhythmias to a time point when the arrhythmias occurred less than one every 30 seconds. S-T segment changes following balloon occlusion were recorded from the isoelectric line either following the P or the T wave from the standardized precordial lead $V_4$.

Myocardial blood flow. Myocardial blood flow was measured using radioactive microspheres. Microspheres were injected as baseline, 60 minutes after occlusion, 5 minutes after the initiation of reperfusion and after 170 minutes of reperfusion. The radioactive microspheres were supplied as carbonized plastic spheres 15.5±3.0 microns in diameter, which were labeled with either $^{153}$Gd, $^{85}$Sr, $^{46}$Sc, or $^{113}$Sn. The isotope is bonded into the carbonized plastic and does not leach from the sphere in saline or plasma. Microspheres (New England Nuclear) were obtained as 1 mCi of nuclide in 10 ml saline, to which 0.05% Tween-80, a surface detergent, was added to minimize aggregation. Twenty $\mu$Ci of the microspheres were removed from the sterile sealed vial with a syringe and diluted in saline to the appropriate concentration. The order of the microsphere injection was randomized to avoid bias of the data from microsphere lot or isotope type. The mixture of spheres was sonicated for at least 30 minutes prior to injection to assure complete dispersal. Immediately before injection, the microspheres were mechanically shaken with a Vortex type mixer. Approximately $1.3 \times 10^6$ microspheres were injected into the animals left ventricle and flushed with saline. In theory, the microspheres mix with the blood ejected from the left ventricle and are transported to the tissue in a similar pattern as red blood cells. The microspheres are trapped by the slightly smaller diameter capillaries ($8\mu$). The spheres remain lodged in the capillary bed with minimal migration until necropsy. To calibrate blood flow, an arterial blood flow sample was collected with a withdrawal rate of 2.06 ml/min during the time interval that the microspheres were infused. Following the determination of the areas at risk and the infarcted tissues the left ventricular tissue slices were subdivided into epicardial, mid-myocardial, and endocardial thirds and the activity of each isotope was determined in a gamma counting system (Searl, Model 1185). Following this counting procedure, the tissue was divided into white, red and blue regions and recounted. The cardiac output and regional myocardial blood flow was calculated for each time point as previously described Heyman, et al., "Blood flow measurement with radionuclide-labeled particles", *Progress in Cardiovascular Disease,* 20:55–79 (1977).

Analysis of myocardium at risk. Immediately after the heart was removed, the first obtuse marginal branch of the circumflex coronary artery was isolated and cannulated. In addition the left main coronary artery was cannulated to allow perfusion of both the left anterior descending and circumflex coronary arteries. Both vessels were simultaneously perfused at 120 mmHg. The marginal branch was perfused with 1.0% triphenyltetrazolium chloride (Sigma) and the left main coronary artery was perfused with 0.05% monastral blue. Triphenlytetrazolium chloride stains viable myocardium red and does not stain areas of necrotic or infarcted tissue. The heart was incubated in saline at 37° C. for 20 minutes to allow staining. The heart was then perfusion fixed with formalin. The mean total weight of the left ventricle was the same for the DCLHb and HSA groups, 55.3±2.3 and 53.1±5.2 grams, respectively.

The heart was sectioned into 0.5 cm thick transverse slices with a mechanical slicer and each slice was weighed. The basilar surface of each slice was photographed. Each photograph was scanned into a MacIntosh computer (Scanjet scanner, Adobe photoshop program) and using a computer-aided planimetric program (NIH Image), the area at risk and the area of infarction were quantitated. The area of infarction was expressed as a percent of the area at risk.

Data Analysis. Data are presented as mean values ±SEM. Differences between groups at single time points were evaluated by the Student's t-test for unpaired data. For groups with significant disparities between standard deviations, nonparametric Mann-Whitney U-statistical analysis was performed. Differences among groups and between groups for multiple data points were compared by analysis of variance. The 0.05 level of significance was used to evaluate the statistical differences.

Hemodynamic Data. Heart rate and mean arterial blood pressure (MAP) remained constant during the first ninety five minutes of the experiment for both DCLHb and HSA treated groups (Table 1). Pigs receiving HSA showed a significant decrease in MAP at the 3 hour reperfusion period. Heart rate showed a significant 30% decrease from control in the DCLHb group at the 3 hour time point. Cardiac output was not significantly different from control during the occlusion or 5 minute reperfusion periods, but was significantly reduced in both the DCLHb and HSA groups at the 3 hour reperfusion period. Cardiac output was not different between the DCLHb and HSA groups at any time point. Calculated total peripheral resistance (TPR) was not significantly different between the DCLHb and HSA groups at either the control or occlusion time intervals. However, the DCLHb group had a significant increase in TPR at 5 minutes and 3 hours of reperfusion.

TABLE 1

HEMODYNAMIC DATA

|  |  | Mean Arterial Blood Pressure, mmHg | Heart Rate beats/min | Cardiac Output liters/min | Total Peripheral Resistance |
|---|---|---|---|---|---|
| Control | DCLHB | 97 ± 7 | 130 ± 10 | 4.3 ± 0.5 | 24 ± 2 |
|  | HSA | 93 ± 5 | 125 ± 14 | 5.0 ± 0.5 | 19 ± 2 |
| Occlusion | DCLHB | 95 ± 10 | 120 ± 14 | 3.4 ± 0.3 | 28 ± 2 |
| (80 min.) | HSA | 98 ± 7 | 111 ± 5 | 3.3 ± 0.3 | 29 ± 1 |
| 5 min. | DCLHB | 114 ± 8 | 127 ± 7 | 3.2 ± 0.3 | 38 ± 4*† |
| Reperfusion | HSA | 94 ± 7 | 106 ± 5 | 4.0 ± 0.3 | 26 ± 1 |
| 3 hrs. | DCLHB | 92 ± 9† | 91 ± 4*† | 2.5 ± 0.4* | 46 ± 8*† |
| Reperfusion | HSA | 74 ± 9* | 125 ± 20 | 3.0 ± 0.2* | 25 ± 4 |

Blood Data. Table 2 shows that arterial pH was not significantly different between any of the time periods in either group. Arterial pH was 7.51±0.01 with a range between 7.46 and 7.54. Although both $PCO_2$ and $PO_2$ remained very stable throughout the experiment, $PCO_2$ was significantly different from the HSA group during 5 minute reperfusion sample interval in the DCLHb treated group. $PO_2$ in the DCLHb group was significantly increased above the HSA group at the occlusion time period.

TABLE 2

BLOOD GAS DATA

|  |  | pH | $PCO_2$ mmHg | $PO_2$ mmHg |
|---|---|---|---|---|
| Control | DCLHb | 7.49 ± .03 | 35 ± 3 | 110 ± 8 |
|  | HSA | 7.5 ± .023 | 40 ± 4 | 89 ± 7 |
| Occlusion | DCLHb | 7.53 ± .02 | 32 ± 2 | 106 ± 4 |
| (80 min.) | HSA | 7.46 ± .02 | 43 ± 3 | 86 ± 6 |
| 5 min. | DCLHb | 7.52 ± .02 | 30 ± 2† | 99 ± 10 |
| Reperfusion | HSA | 7.5 ± .034 | 40 ± 2 | 83 ± 7 |
| 3 hrs. | DCLHb | 7.54 ± .03 | 32 ± 3 | 96 ± 14 |
| Reperfusion | HSA | 7.5 ± .041 | 37 ± 3 | 76 ± 8 |

NOTE FOR TABLE 2:
Values are mean ± SEM.
*Indicates significant difference from control ($P < 0.05$).
†Indicate significant difference from HSA.

Figure 1B:
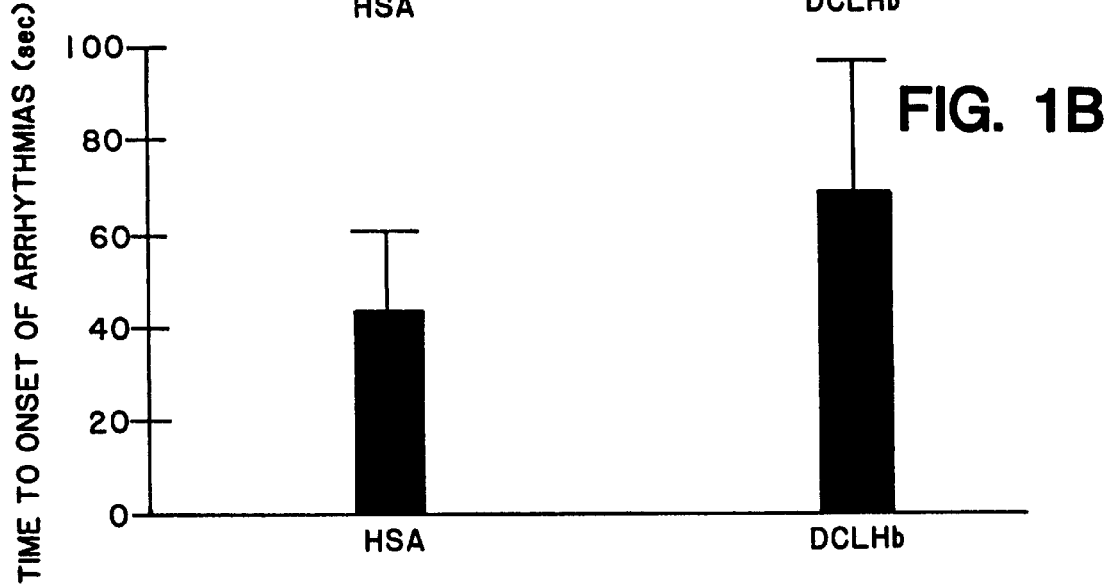
FIG. 1B. Effects of human serum albumin (HSA) and diaspirin crosslinked hemoglobin (DCLHb™) on the time to onset of reperfusion arrhythmias. The time in seconds is measured from beginning of reperfusion to the first series of reperfusion arrhythmias. Values are means ±SEM.
Figure 1C:
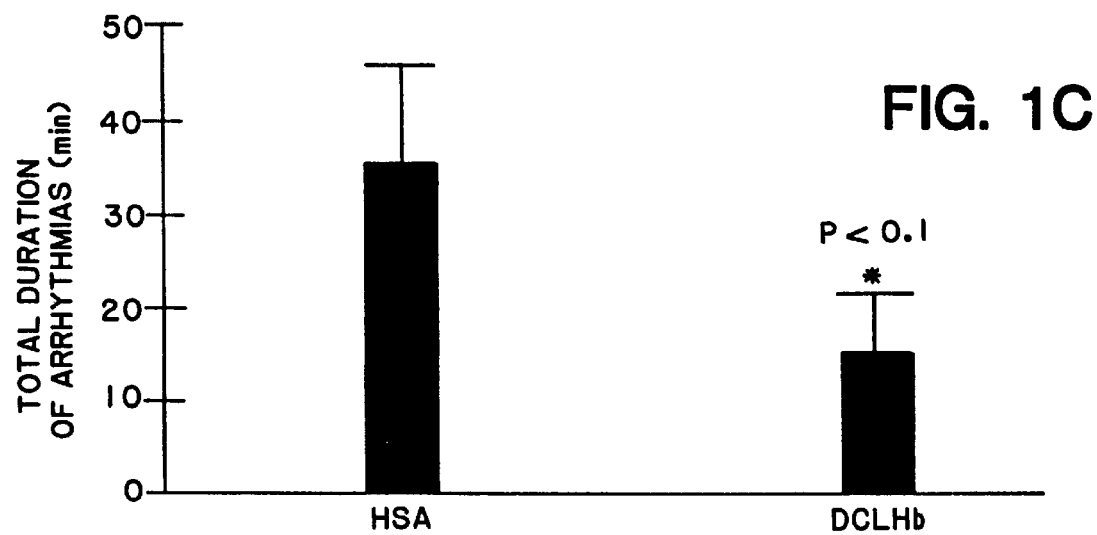
FIG. 1C. Effects of human serum albumin (HSA) and diaspirin crosslinked hemoglobin (DCLHb™) on the total duration of reperfusion arrhythmias. The time in minutes of arrhythmias are counted from beginning of the first accelerated idioventricular beat to a time when the arrhythmias occurred less than one every 30 seconds. Values are means ±SEM. *Significantly different from HSA (P<0.10).
Figure 2:
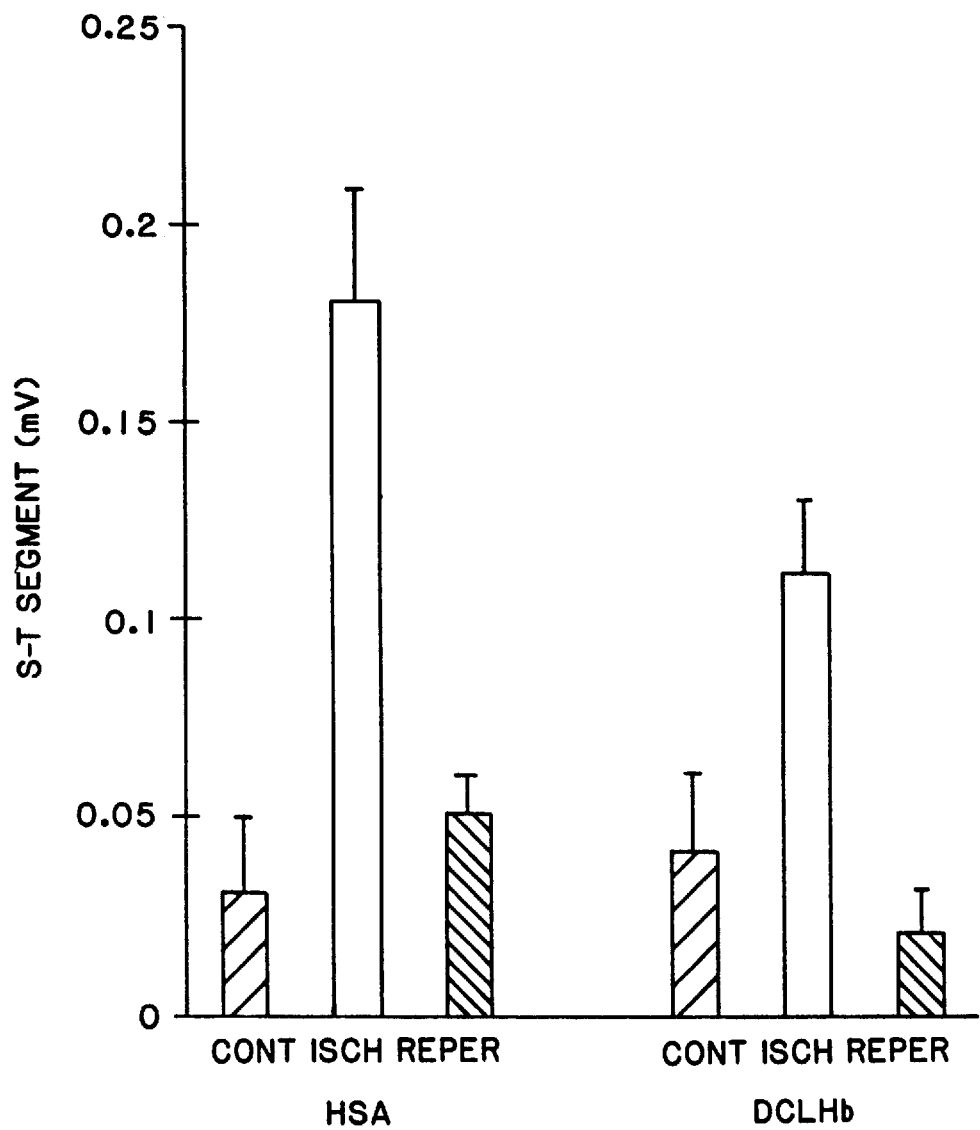
FIG. 2. S-T Segment changes (mVolts) in HSA and DCLHb treated groups. Control (Cont) is prior to balloon occlusion. Ischemia (Isch) is 80 minutes into ischemia prior to HSA or DCLHb infusion. Reperfusion is 3 hours into the reperfusion period.

ECG Data. Reperfusion arrhythmias were noted in both the DCLHb and HSA groups (FIG. 1); however, the total number of reperfusion arrhythmias, from start of reperfusion to 45 minutes post-reperfusion, was greater in the HSA group (1274±222) than the DCLHb group (437±198). The time to onset of arrhythmias (DCLHb, 67.5±28.4 seconds; HSA, 43.7±17.0 seconds) and the total duration of the arrhythmic period (DCLHb, 14.5±6.5 minutes; HSA, 35.2±10.9 minutes) were not statistically different for the two groups; however, there was a trend for DCLHb to increase the time to onset and to decrease the total duration of the arrhythmic period. Balloon occlusion produced a significant ST segment elevation from control in both groups (DCLHb, 0.11±0.02 mV; HSA, 0.18±0.03 mV) (FIG. 2). There was no statistical difference between the two groups with regard to ST segment elevation during the occlusion or 3 hour reperfusion time period. DCLHb had reduced the ST segment elevation to 0.02±0.01 mV while the HSA treated animals still showed a 0.05±0.01 mV ST segment change.

Blood Flow Data. Myocardial blood flow data are presented in Tables 3A and 3B. Table 3A shows blood flow to the epicardium, mid myocardium, endocardium and the endocardial:epicardial (endo/epi) blood flow ratio to an area of the free wall of the left ventricle that was not at risk for ischemia or infarction. We routinely examined tissue from the posterior wall of the left ventricle that was not perfused by the circumflex vessel. There were no differences in myocardial blood flow or endo/epi ratios with the exception of at the 3 hour reperfusion time interval in the DCLHb treated group, which exhibited a significant reduction in epicardial blood flow from control. Table 3B demonstrates the same parameters in tissue that is at risk for infarction. These blood flow measurements include tissue from both the ischemic area (white) and the area which was at risk but not ischemic (red). There was no significant difference between tissues of this region and the tissues in Table 3A during the control measurement period. The occlusion period produced a significant reduction in blood flow to all three regions of the myocardium in tissue at risk in pigs treated with either DCLHb or HSA. The endo/epi ratio was increased in both DCLHb and HSA groups during occlusion, indicating a proportionally greater reduction in blood flow to the epicardial region as compared to the endocardial layer of the myocardium. During the 5 minute reperfusion time period, there was a dramatic hyperemia to epi, mid, and endocardial tissue in both DCLHb and HSA groups with the exception of the endocardial region in the HSA group. The endo/epi ratio was therefore significantly less than that in the control ratio. Blood flows returned to control values at the 3 hour reperfusion period with the exception of the flow to the epicardial region in the DCLHb treated group. In this sample there was a significant difference in the pigs receiving DCLHb from control values and from the same tissue in the HSA treated group. Table 4 shows myocardial blood flow from the same hearts as included in Tables 3A and B, but this tissue has been divided into areas that were stained red (area at risk but not infarcted), tissues that were white (areas that did not take up the stain, therefore this area was infarcted) and the total combined flow to this region. Flow fell significantly to these regions during occlusion. The flow to the area at risk is defined as the collateral blood flow and was not significantly different between DCLHb and HSA. (See FIG. 3). Since this flow was measured prior to treatment, these two flows should be similar. During occlusion the infarcted area showed tissue flows that were not significantly different from zero. The 5 minute reperfusion data demonstrate significant active hyperemia to all tissues in both DCLHb and HSA treated groups and there was no difference between flows in the two groups. At the 3 hour time point, blood flow to both the area at risk and the infarcted tissue in the DCLHb treated group was significantly reduced from control values while the corresponding flows in HSA treated animals had returned to control values.

TABLE 3A

MYOCARDIAL BLOOD FLOW, ml/min/100 g
(Tissue Not in Area at Risk)

|  |  | EPI | MID | ENDO | ENDO/EPI |
|---|---|---|---|---|---|
| Control | DCLHb | 171 ± 31 | 195 ± 33 | 212 ± 38 | 1.3 ± 0.2 |
|  | HSA | 143 ± 17 | 167 ± 19 | 180 ± 18 | 1.3 ± 0.1 |
| Occlusion | DCLHb | 135 ± 23 | 143 ± 21 | 160 ± 16 | 1.3 ± 0.1 |
| (80 min.) | HSA | 117 ± 16 | 144 ± 20 | 154 ± 20 | 1.3 ± 0.1 |
| 5 min. | DCLHb | 147 ± 18 | 188 ± 26 | 200 ± 22 | 1.4 ± 0.1 |
| Reperfusion | HSA | 139 ± 17 | 165 ± 19 | 174 ± 21 | 1.3 ± 0.1 |
| 3 hrs. | DCLHb | 89 ± 15* | 113 ± 20 | 130 ± 17 | 1.5 ± 0.1 |
| Reperfusion | HSA | 105 ± 18 | 126 ± 24 | 142 ± 26 | 1.4 ± 0.1 |

TABLE 3B

MYOCARDIAL BLOOD FLOW, ml/min/100 g
(Ischemic Tissue)

|  |  | EPI | MID | ENDO | ENDO/EPI |
|---|---|---|---|---|---|
| Control | DCLHb | 181 ± 28 | 188 ± 30 | 217 ± 39 | 1.2 ± 0.1 |
|  | HSA | 152 ± 19 | 176 ± 23 | 202 ± 24 | 1.3 ± 0.1 |
| Occlusion | DCLHb | 81 ± 15* | 92 ± 19* | 121 ± 20* | 1.6 ± 0.1* |
| (80 min.) | HSA | 60 ± 14* | 78 ± 17* | 117 ± 22* | 2.1 ± 0.2* |
| 5 min. | DCLHb | 325 ± 29* | 308 ± 24* | 312 ± 29* | 1.0 ± 0.1 |
| Reperfusion | HSA | 301 ± 33* | 292 ± 42* | 268 ± 35 | 0.9 ± 0.1* |
| 3 hrs. | DCLHb | 95 ± 15*† | 102 ± 19 | 119 ± 18 | 1.3 ± 0.1 |
| Reperfusion | HSA | 157 ± 36 | 168 ± 37 | 179 ± 35 | 1.2 ± 0.2 |

NOTE FOR TABLE 3B:
Values are means ± SEM.
*Indicates significant difference from control ($P < 0.05$).
†Indicates significant difference from HSA ($P < 0.05$).
EPI = Epicardial tissue,
MID = middle ⅓ of Myocardial tissue,
ENDO = Endocardial tissue.
ENDO/EPI represents the ratio of endocardial blood flow to epicardial blood flow.

TABLE 4

MYOCARDIAL BLOOD FLOW (ml/min/100 g)
TO AREA AT RISK AND AREA INFARCTED

|  |  | Area at Risk | Area Infarcted | TOTAL |
|---|---|---|---|---|
| Control | DCLHb | 242.09 ± 49.04 | 178.64 ± 37.20 | 210.78 ± 40.68 |
|  | HSA | 234.95 ± 34.23 | 176.15 ± 32.42 | 203.30 ± 34.96 |
| Occlusion | DCLHb | 86.02 ± 10.89* | 2.45 ± 0.80* | 57.21 ± 12.05* |
| (80 min.) | HSA | 79.62 ± 16.55* | 9.94 ± 3.18* | 55.54 ± 14.57* |
| 5 min. | DCLHb | 514.89 ± 90.85* | 390.79 ± 64.69* | 441.65 ± 70.75* |
| Reperfusion | HSA | 522.01 ± 71.64* | 313.84 ± 58.64* | 407.02 ± 64.50* |
| 3 hrs. | DCLHb | 121.29 ± 19.27*† | 102.86 ± 22.36* | 105.74 ± 13.93* |
| Reperfusion | HSA | 233.93 ± 49.06 | 166.00 ± 45.48 | 196.85 ± 48.27 |

NOTE FOR TABLE 4:
Values are means ± SEM.
*Indicates significant difference from control ($P < 0.05$).
†Indicates significant difference from HSA.
Column one "Area at Risk" is total collateral blood flow during occlusion.
Column two "Area Infarcted" is the area of no flow only.
Column three is the flow to the entire area of infarction plus area at risk.

TABLE 5

KIDNEY BLOOD FLOW (ml/min/100 g)

|  |  | LEFT | RIGHT | TOTAL |
|---|---|---|---|---|
| Control | DCLHb | 276 ± 53 | 292 ± 51 | 284 ± 51 |
|  | HSA | 330 ± 27 | 315 ± 34 | 323 ± 30 |
| Occlusion | DCLHb | 265 ± 34 | 278 ± 35 | 271 ± 34 |
| (80 min.) | HSA | 299 ± 07 | 291 ± 13 | 295 ± 09 |
| 5 min. | DCLHb | 237 ± 28 | 253 ± 25 | 244 ± 26 |
| Reperfusion | HSA | 331 ± 30 | 334 ± 30 | 338 ± 26 |
| 3 hrs. | DCLHb | 206 ± 29 | 223 ± 33 | 214 ± 30 |
| Reperfusion | HSA | 324 ± 46 | 311 ± 53 | 317 ± 48 |

NOTE FOR TABLE 5:
Values are means ± SEM.
None of the values listed are different from control nor are there differences between treatment groups. There are no differences between right and left kidney flows.

Table 5 demonstrates that in an anatomically paired organ, microspheres were equally distributed between the left and right kidney and that there was no significant difference between renal blood flow between the DCLHb and the HSA treated groups. These measurements are presented to validate the microsphere technique in this model.

TABLE 5-continued

KIDNEY BLOOD FLOW (ml/min/100 g)

|  | LEFT | RIGHT | TOTAL |
|---|---|---|---|

LEFT = Left Kidney Flow,
RIGHT = Right Kidney Flow,
TOTAL = Total Kidney Flow.

Infarction Data. Infarct size and areas at risk in DCLHb and HSA treated hearts are shown in Table 6. The percent of the total left ventricle that was at risk was 14.6±2.6% for the DCLHb group and 10.6±2.1% for the HSA group. These values were not significantly different. The total area at risk was 1126±218 mm$^3$ and 858±173 mm$^3$ for DCLHb and HSA treated groups respectively. The total infarcted area for DCLHb was 326±91 mm$^3$ and 456±101 mm$^3$ for HSA. These data then yield the percent of infarcted tissue as compared to the area at risk. In the DCLHb group 30.9±6.1% of the area at risk was infarcted, while in the HSA group 53.2±1.9% of the area at risk was infarcted. Since this is a ratio, the data were subjected to an Arcsine transformation for the statistical analysis. The DCLHb group was statistically different from the HSA group at P<0.009 using an unpaired t-test.

Figure 3:
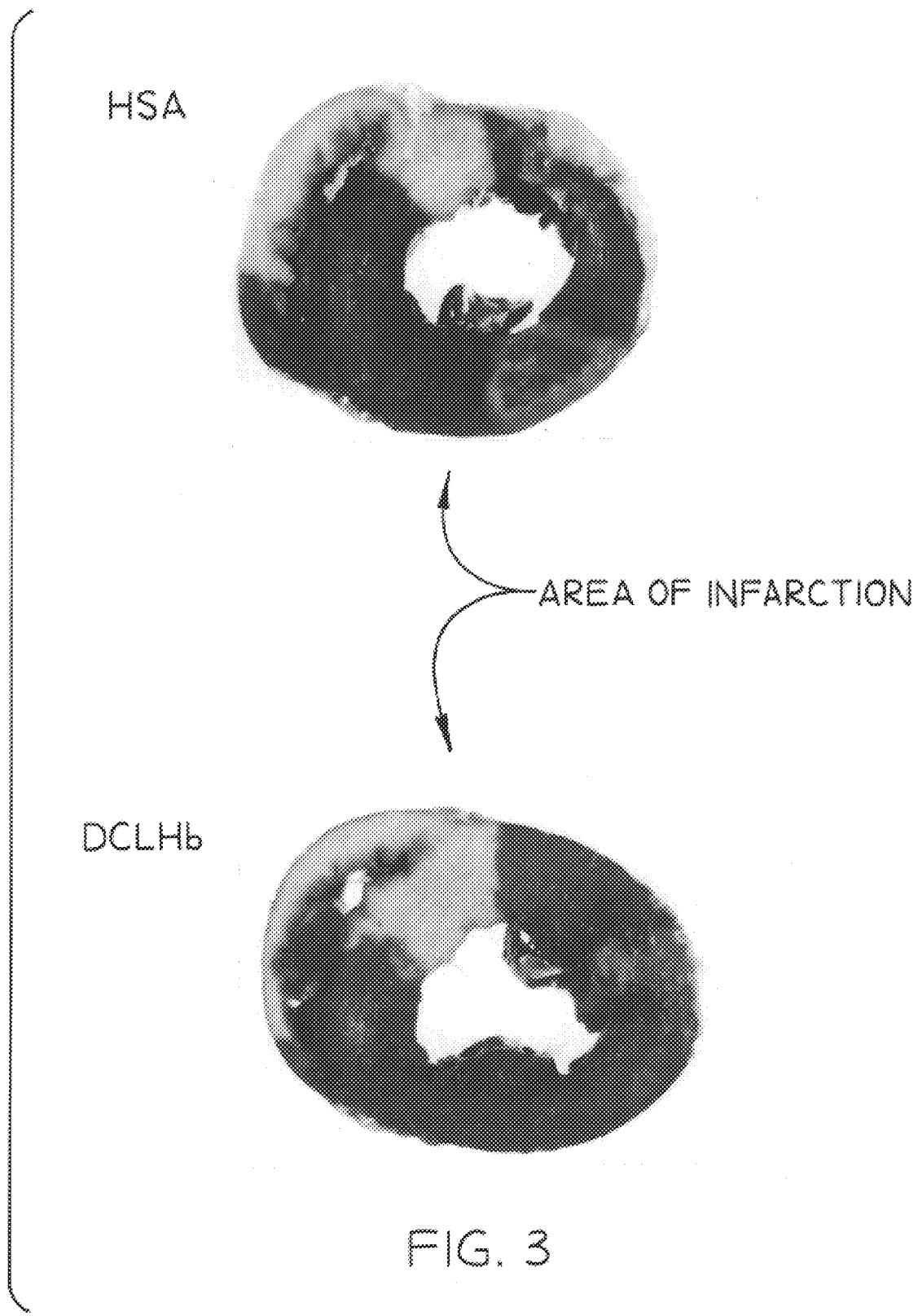
FIG. 3. Photograph comparing the infarct size in transverse cross-section between DCLHb and HSA infused test animals.

Intravenous infusion of DCLHb eighty minutes following occlusion of the first obtuse marginal branch of the circumflex coronary artery of the pig produced a significant reduction in the size of myocardial infarction compared to control animals which were infused with an oncotically matched human serum albumin solution. In addition, DCLHb significantly reduced detrimental reperfusion arrhythmias and produced a hemodynamically stable animal. FIG. 3 shows transverse tissue sections through the swine myocardium. Comparative of the stained (vital) areas in the DCLHb and HSA perfused heart shows that the area of infarct is much smaller in the DCLHb perfused heart.

The myocardial blood flow data, as measured by radioactive microspheres, can not account for the reduced infarction size in the DCLHb group. The only difference between the DCLHb and the HSA groups is the reduced epicardial blood flow and reduced blood flow to the area at risk in the DCLHb group at the 3 hour reperfusion time point. Reduction in flow at this time point should not correlate with an improvement in oxygen delivery and a reduction in infarction size.

TABLE 6

INFARCTION DATA

|  | % of LEFT VENTRICLE AT RISK | TOTAL AREA AT RISK mm$^3$ | TOTAL AREA INFARCTED mm$^3$ | % OF THE AREA AT RISK INFARCTED |
|---|---|---|---|---|
| DCLHb | 14.6 ± 2.6 | 1126 ± 218 | 326 ± 91 | 30.9 ± 6.1† |
| HSA | 10.6 ± 2.1 | 858 ± 173 | 456 ± 101 | 53.2 ± 1.9 |

NOTE FOR TABLE 6:
Values are means ± SEM.
†Indicates significant difference from HSA (P < 0.05).

What is claimed is:

1. A method for reducing reperfusion injury in tissue whose nourishment has been disrupted by blockage of a blood vessel, comprising administering stroma-free, diaspirin-crosslinked hemoglobin to an ischemic patient at risk for developing reperfusion injury.

2. The method of claim 1 wherein the hemoglobin is administered as soon as possible after the patient is diagnosed as having blockage of a blood vessel.

3. The method of claim 1 wherein the patient at risk for developing reperfusion injury has suffered ischemia for more than one hour.

4. The method of claim 1 wherein the patient is a human.

5. The method of claim 1 wherein the hemoglobin is a physiologically acceptable solution containing from about 10 milligrams hemoglobin per kilogram body weight to about 2,500 milligrams hemoglobin per kilogram body weight.

6. The method of claim 1 wherein the hemoglobin is a physiologically acceptable solution and is administered to a patient until the patient's mean arterial blood pressure is about 5% to 15% greater than a preadministration value.

7. A method for reducing reperfusion injury in tissue whose nourishment has been disrupted by blockage of a blood vessel, comprising administering a hemoglobin preparation containing from about 10 milligrams stroma-free, diaspirin-crosslinked hemoglobin per kilogram body weight to about 2,500 milligrams stroma-free, diaspirin-crosslinked hemoglobin per kilogram body weight to an ischemic patient at risk for developing reperfusion injury.

8. The method of claim 7 wherein the hemoglobin preparation is administered as soon as possible after the patient is diagnosed as having blockage of a blood vessel.

9. The method of claim 7 wherein the patient at risk for developing an infarction has suffered ischemia for more than one hour.

10. The method of claim 7 wherein the patient is a human.

11. The method of claim 7 further including the step of removing the blockage from the blood vessel of the patient to reestablish blood flow to the tissue.

* * * * *